United States Patent
Witty et al.

(10) Patent No.: US 7,192,777 B2
(45) Date of Patent: *Mar. 20, 2007

(54) APPARATUS AND METHOD FOR PROCESS MONITORING

(75) Inventors: Thomas R. Witty, Santa Cruz, CA (US); Robert Case, Henderson, NV (US)

(73) Assignee: Fastraq, Inc., Henderson, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/099,707

(22) Filed: Apr. 5, 2005

(65) Prior Publication Data

US 2005/0186682 A1    Aug. 25, 2005

Related U.S. Application Data

(62) Division of application No. 10/845,767, filed on May 14, 2004.

(60) Provisional application No. 60/470,725, filed on May 14, 2003.

(51) Int. Cl.
*G01N 35/02* (2006.01)
*G01N 35/08* (2006.01)
*G01N 33/18* (2006.01)
*G01N 33/48* (2006.01)
*G01N 33/72* (2006.01)

(52) U.S. Cl. ............ 436/50; 436/43; 436/52; 436/53; 436/63; 436/66; 436/149; 436/167; 436/172; 436/164; 436/165; 436/171; 422/50; 422/52; 422/55; 422/61; 422/62; 422/63; 422/68.1; 422/69; 422/73; 422/81; 422/82; 422/82.01; 422/82.02; 422/82.03; 422/82.08; 422/82.09; 422/99; 422/100; 422/101; 422/102; 422/103; 422/104; 73/1.01; 73/1.02; 73/53.01

(58) Field of Classification Search .......... 422/50, 422/52, 55, 57, 58, 61, 62, 63, 68.1, 69, 73, 422/81, 82, 82.01, 82.02, 82.03, 82.08, 82.09, 422/99, 100, 101, 102, 103, 104; 436/43, 436/52, 53, 63, 66, 149, 169, 172, 513, 518, 436/50, 164, 165, 171; 435/287.1, 287.2, 435/287.7, 287.9; 73/1.01, 1.02, 53.01
See application file for complete search history.

(56) References Cited

U.S. PATENT DOCUMENTS

| | | | |
|---|---|---|---|
| 4,222,744 A | | 9/1980 | McConnell |
| 5,965,456 A | * | 10/1999 | Malmqvist et al. ......... 436/514 |
| 6,002,475 A | * | 12/1999 | Boyd et al. ................. 356/246 |
| 6,218,719 B1 | | 4/2001 | Tsang |
| 6,222,619 B1 | | 4/2001 | Herron et al. |
| 6,228,652 B1 | | 5/2001 | Rodriguez et al. |

(Continued)

Primary Examiner—Brian Sines
(74) Attorney, Agent, or Firm—Paul Davis; Heller Ehrman LLP

(57) ABSTRACT

An apparatus is provided for testing fluid samples includes a sensor, which can be light source, directed to a flow cell and a photo sensor for detecting a light beam reflected from the flow cell. The photo sensor monitors the fluid in the flow cell by sensing the reflected light beam from the flow cell, thereby monitoring the test process. The apparatus may have additional light source so that the photo sensor may monitor the test process by detecting the absorption light beam or fluorescent light beam from the flow cell at different phases of the test process.

36 Claims, 7 Drawing Sheets

U.S. PATENT DOCUMENTS

| | | |
|---|---|---|
| 6,326,612 B1 | 12/2001 | Elkind |
| 6,524,858 B1 | 2/2003 | Zelmanovic et al. |
| 6,592,822 B1 | 7/2003 | Chandler |
| 6,611,634 B2 * | 8/2003 | Herron et al. ............... 385/12 |
| 6,692,696 B1 | 2/2004 | Alberte |
| 2002/0128234 A1 * | 9/2002 | Hubbell et al. ............ 514/100 |

* cited by examiner

APPARATUS AND METHOD FOR PROCESS MONITORING

CROSS-REFERENCE TO RELATED APPLICATIONS

This application is a divisional of U.S. Ser. No. 10/845,767 filed May 14, 2004, which claims the benefit of U.S. Ser. No. 60/470,725, filed May 14, 2003. Both of the above applications are fully incorporated herein by reference.

BACKGROUND OF THE INVENTION

1. Field of the Invention

The present invention relates generally to methods and systems for real time process monitoring and, more specifically, to methods and systems for monitoring chemical or biological test process.

2. Description of the Related Art

Blood and other body fluid tests are important diagnostic methods in patient care and treatment. The reliability and the accuracy of the tests are critical in correctly diagnosing the patient and administrating proper treatment. The Food and Drug Administration (FDA) has established numerous quality standards for the various blood or body fluid tests. Monitoring the test process is beneficial in producing reliable and accurate test results.

One way of monitoring the test process is periodically performing the monitoring test on standard test samples. The monitoring test results are compared with expected results to verify the accuracy of the test processes or correct the test instrument or process when appropriate. In this approach, the test processes are assumed to generate consistent result between the monitoring tests.

Another way of monitoring the test process is including standard test samples in the test process. This approach is suitable for a test process that performs tests on multiple samples. The test results on the standard test samples are compared with expected results to verify the accuracy of the test processes. In this approach, the test processes on real samples are assumed to generate result consistent with those on standard test samples.

These monitoring processes are time and cost inefficient. They are deficient in meeting the needs of point of care, e.g., emergency room, test processes. In addition to being reliable and accurate, an emergency room test process should be simple to operate and generate results fast.

Accordingly, it would be advantageous to have an apparatus and a method for monitoring a test process that is continuous, simple, and reliable. It is desirable for the test apparatus to be compact and capable of generating test results fast thereby meeting the need of the emergency rooms. It would be of further advantage for the apparatus and method to be easily adaptable for monitoring different test processes.

SUMMARY OF THE INVENTION

An object of the present invention is to provide improved methods and systems for monitoring a test processes in real time.

Another object of the present invention is to provide methods and systems for monitoring test processes that performs a comparison of a timing of the introduction, and the exit of a sample to and from a measurement chamber, in order to confirm of a point in time of a valid reaction of the sample in the measurement chamber.

Yet another object of the present invention is to provide methods and systems for monitoring test processes that directly monitors the flow of a sample and a reagent into a measurement chamber.

A further object of the present invention is to provide methods and systems for monitoring test processes in a flow cell that in real time sense the flow a sample or a reagent without relying on information that originates outside the flow cell.

These and other objects of the present invention are achieved in an apparatus for testing fluid samples. A flow cell is adapted to be positioned in a flow cell support. The flow cell includes a reaction chamber. A monitor device monitors and produces a signal that is indicative of an introduction and an exit of a sample to and from the reaction chamber. Logic resources receive the signal and perform a comparison of a timing of the introduction and the exit of the sample to and from the reaction chamber. This produces a confirmation of a point in time for a valid reaction of the sample in the reaction chamber. An energy source produces an output of energy that interacts with the reaction chamber. A sensor is positioned to receive an output from the flow cell.

In another embodiment of the present invention, a method is provided for determining the presence of at least one biological analyte that may be present in a liquid sample. An apparatus is provided for testing fluid samples that includes a flow cell with a reaction chamber, a monitor device that directly monitors flow of a sample and a reagent into the reaction chamber, a light source that produces an incident beam directed to the reaction chamber; and a sensor positioned to receive an output beam from the flow cell. The liquid sample is introduced into the flow cell. Flow of a sample and a reagent into the reaction chamber is directly monitored in real time without relying on extrinsic information.

DETAILED DESCRIPTION OF VARIOUS EMBODIMENTS

Figure 1:
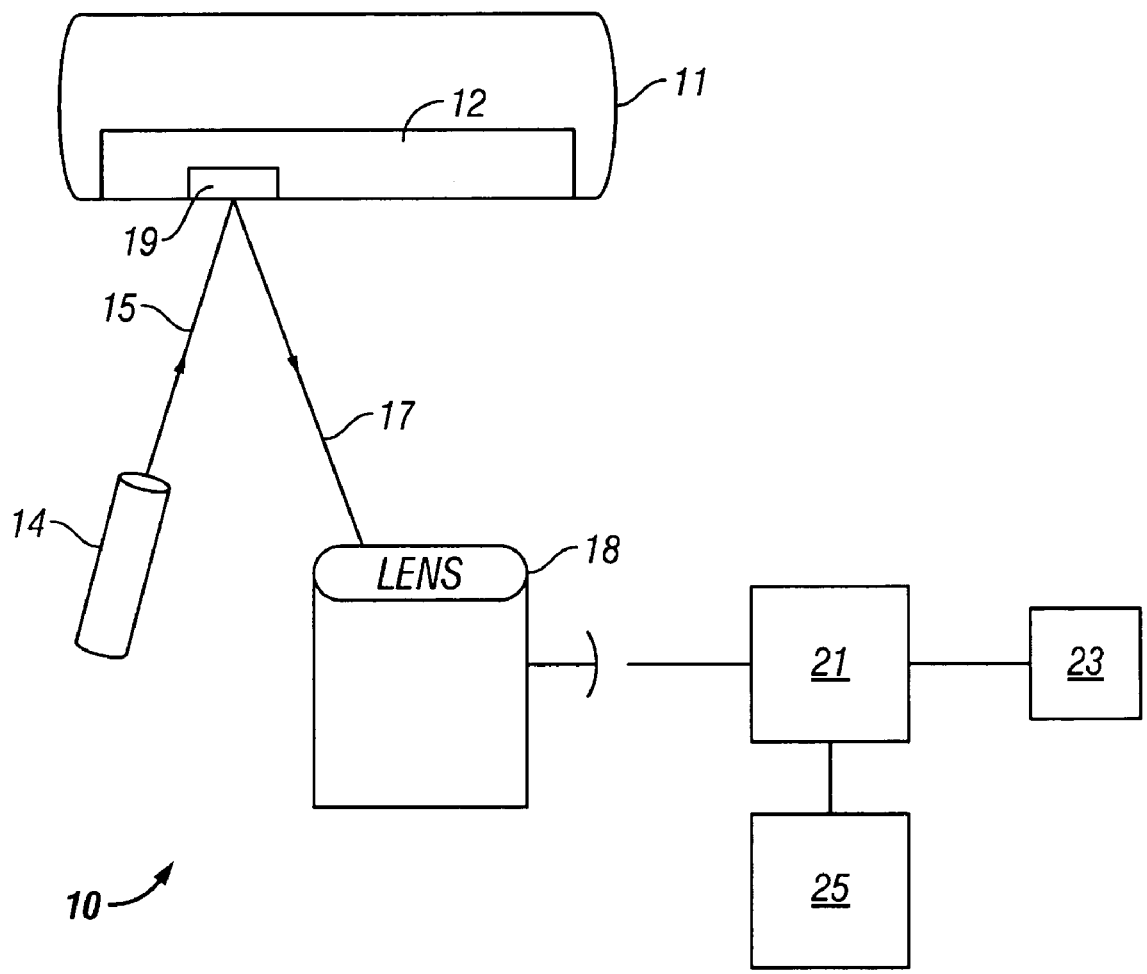
FIG. 1 illustrates an apparatus for performing a test on a fluid sample in accordance with the present invention.

Various embodiments of the present invention are described hereinafter with reference to the figures. Elements of like structures or function are represented with like reference numerals throughout the figures. The figures are only intended to facilitate the description of specific embodiments of the invention. They are not intended as an exhaustive description of the invention or as a limitation on the scope of the invention. They are not necessarily drawn to scale. In addition, an aspect described in conjunction with a particular embodiment of the present invention is not necessarily limited to that embodiment and can be practiced in conjunction with any other embodiments of the invention.

FIG. 1 is a schematic diagram of an apparatus 10 for performing a test on a fluid sample in accordance with the present invention. In accordance with one embodiment, apparatus 10 is used for performing tests on blood samples. The blood tests may be hematology tests, chemistry tests or immunology tests that provide valuable information in diagnosing such conditions as viral infection, bacterial infection, blood loss, heart attack, pregnancy, hormonal disorders, metabolic status, neuronal damage, cancer, cellular function, genetic information, electrolyte balance, blood clotting and the like.

In accordance with the present invention, apparatus 10 is capable of monitoring the blood test process on an effective real time basis without relying on extrinsic information such as the test results of standard samples or secondary process monitoring such as motor position detection.

Apparatus 10 includes a flow cell holder 11 for holding flow cell 12. During a test, the sample flows through flow cell 12. In one embodiment, a reactive antibody specific to an analyte in the test is coated on the surface of flow cell 12 during the production of flow cell 12. For each test, a new flow cell 12 is placed on flow cell holder 11. A sensing of a sample or a reagent is provided in real time without relying on information that originates outside flow cell 12. The external monitoring information can include a mechanical, electrical or photo event within apparatus 10 external to flow cell 12. By way of illustration, and without limitation, the mechanical information can include pump driver movement, valve encoder rotation within apparatus 10, electrical sensing of a sample in a sampling device such as by a needle or other capillary, and the like.

For purposes of this specification, in real time means a frequency of measurement to insure that the reaction in a selected time period has taken place. By way of example, and without limitation, the selected time period can be 10% or less of the overall time period step or process in the reaction. By way of illustration, and without limitation, in real time can be in the range of 1 second to 1 minute, and the like, depending on the analyte and process involved.

Flow cell 12 can also include at least one reactive binding partner, including but not limited to an antibody and the like. The reactive binding partner can be any material that can specifically bind the analyte directly or indirectly. The reactive antibody can be present on a surface of flow cell 12, in a flow path of flow cell 12 (which can be in the form of on a membrane, on particles immobilized in the flow path, and the like. The reactive binding partner can immobilized in a flow path of flow cell 12. Samples and/or reagents are into flow cell 12, The reagent can be a calibrant, a fluid containing reactant, a fluid not containing a reactant, a sample, and the like.

For optical detection ease, one or more dyes can be included and mixed with the reactive binding partner. Electrical and other means of sensing can be aided with other non-interfering additives. The inclusion of dye base line image data with different characteristics can be utilized. By way of illustration, and without limitation, the different characteristics can be different in intensity, frequency, magnetic field or other measureable property.

Apparatus 10 also includes an energy source 14 that can be positioned adjacent to flow cell holder 11 A sensor 18 is positioned to receive an output from flow cell 12. In accordance with one embodiment of the present invention, Energy source 14 can be a variety of different sources including but not limited to electrical, mechanical, optical (both coherent and incoherent light), RF, resistive heating, ultrasound, magnetic, and the like.

When energy source 14 is optical, energy source 14 can be a LED or LED array. Suitable LED's include but are not limited to, white, red, green, blue source, and the like. An electromagnetic field can also be utilized. As a light source, energy source 14 can be positioned to project an incident light beam 15 towards flow cell 12. In response to the activity in flow cell 12, a light beam 17 is reflected from flow cell 12. More than one light source 14 can be used. Multiple light sources 14 can be employed to monitor different test processes using image data formed from different light beams.

In one embodiment, apparatus 10 flow cell 12 includes a measurement chamber 19. A monitor device 21 directly monitors and produces a signal indicative of an introduction and an exit of at least one of a sample or a reagent to and from measurement chamber 19. Logic resources 23 receive the signal and performs a comparison of a timing of the introduction and the exit of the sample to and from measurement chamber 19. This produces a confirmation of a point in time of a valid reaction of the sample in measurement chamber 19. The validity of the reaction is defined by the juxtapositioning of two or more reagents in a timeframe that has been determined to be sufficient for full and complete reaction.

Flow cell 12 includes an inlet, an outlet and a channel coupled to measurement chamber 19. Inlet is configured to provide for introduction of the sample into the inlet by a variety of means including but not limited to, laminar flow, absorption, with the use of a pump, and the like.

In one embodiment, flow cell 12 includes bibulous materials. At least a portion of the flow of flow cell 12 can be induced by the bibulous material and is open to the atmosphere. Flow cell 12 can also include non-bibulous materials. In one embodiment, the non-bibulous materials include a surface that has measurement chemistry and a second surface that is filled to the first surface. The second surface provides a window viewable by the sensor, optically or electronically.

A variety of sensors 18 can be utilized, including but not limited to a, photo sensor, charge coupled device, photo detector or array, PMT, CMOS, and the like.

Sensor 18 can be coupled to a digital image processing circuit. Sensor 18 is used to detect changes of the sample in measurement chamber 19. Such optical changes include but are not limited to, light reflection characteristics, light absorption characteristics, and light fluorescence characteristics. Electrical changes include but are not limited to conductance, capacitance, impedance, magnetic disturbances, and the like. In one specific embodiment, sensor 18 is a charge coupled device (CCD) photo detector array coupled to a digital image processing circuit 25. Sensor 18 may also include a light beam focusing lens in front of the CCD photo detectors 18.

Energy source 14 produces an output of energy that interacts with measurement chamber 19. Sensor 18 is positioned to receive an output from flow cell 12. The output can be light intensity, a measurement of wavelength, a measurement of electric capacitance, a measurement of conductivity, impedance and/or magnetic field, and the like.

Monitor device 21 can include energy source 14 and/or sensor 18. Monitor device 21 can directly monitor a progress of events inside measurement chamber 19. This progress of events in measurement chamber 19 includes but is not limited to, sample introduction, calibrant introduction, sample wash out, calibrant displacement, reagent introduction, and the like. In one embodiment, the preceding in the prior sentence occur in a determined order and timing sequence that is dependent on the assay and sensor type.

In one embodiment, monitor device 21 provides an indication of a response of the sample to a mechanical change of apparatus 10. Such a mechanical change can include, but is not limited to, movement of a pump to create a flow of sample or reagent, movement of a reaction area in measurement chamber 19, movement of measurement chamber 19, a mechanical response relative to a secondary reaction in measurement chamber 19, and the like.

In one embodiment, monitor device 21 detects changes in measurement chamber 19, and in response to the changes, determines if there is a sufficient amount of at least one of sample, reagent, calibrant, and the like in measurement chamber 19.

Logic resources 23 can implement a variety of different QC protocols for apparatus 10, as illustrated in FIGS. 2–5, including but not limited to, optical measurement to assure wetting of a strip test area at a selected time, optical measurement to assure wetting of a strip test area in measurement chamber 19 at a selected time following application of pressure to a sample pressurization, optical measurement of flow path to assure sample movement to specific point in a flow path at predetermined time from sample pressurization, optical measurement of a flow path to assure sample removal from a specific point in a flow path and replaced by a diluent at a predetermined time from diluent pressurization, optical measurement of an assay cell in measurement chamber 19, optical measurement of an assay cell in measurement chamber 19 to assure that diluted sample arrives at a selected measurement region and at a selected time from mixed sample pressurization, electrical measurement of an assay cell to assure that a calibrant has sufficiently filled measurement chamber 19, electrical measurement of an assay cell to assure that a calibrant has sufficiently filled measurement chamber 19 by a selected time from calibrant pressurization, electrical measurement of the assay cell to assure that the sample has sufficiently filled the chamber by a selected time from sample accualization, mechanical changes, such as pressure, weight and the like, that can be measured electronically, and the like.

Figure 2:
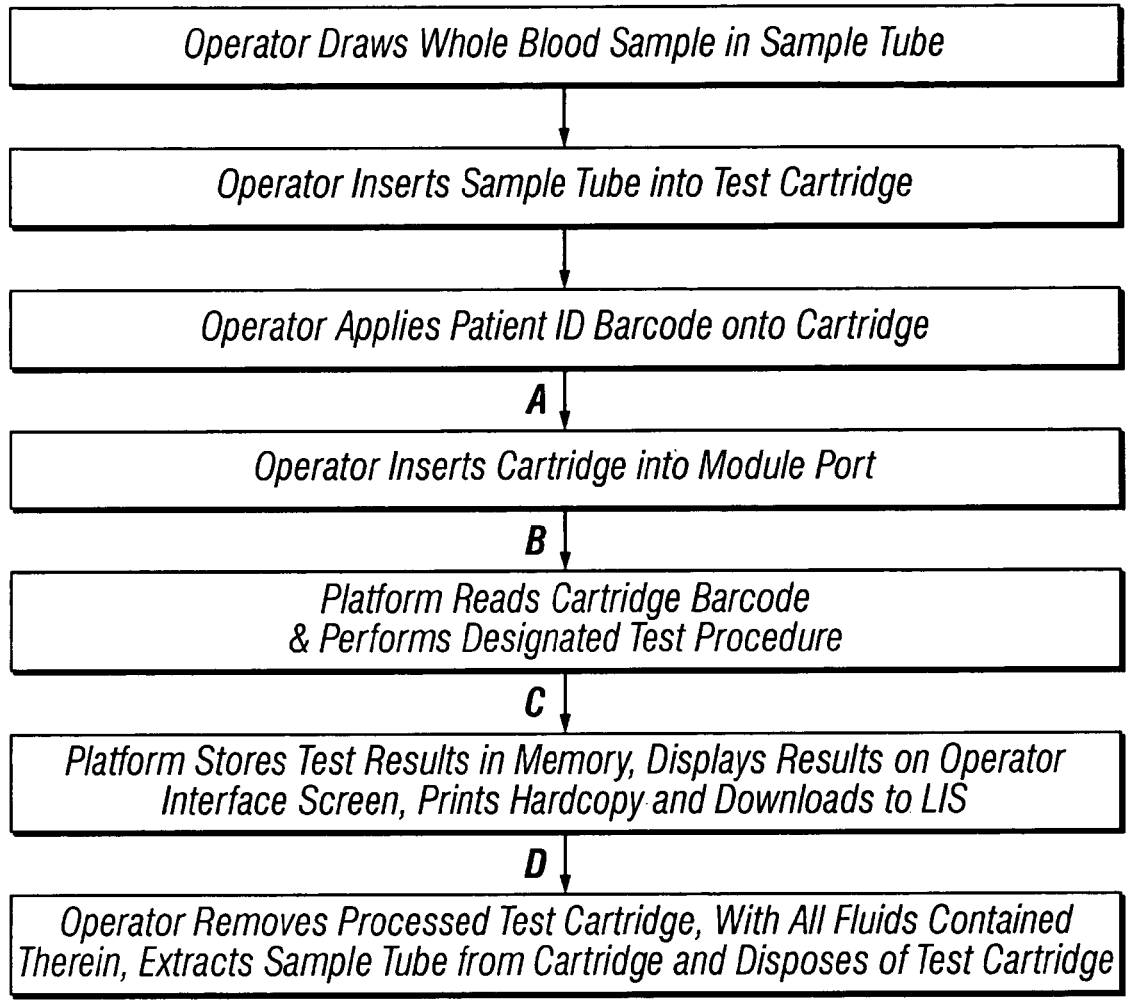
FIG. 2 is a flow chart illustrating one embodiment of an overall methodology implemented by logic resources of the present invetion.
Figure 3:
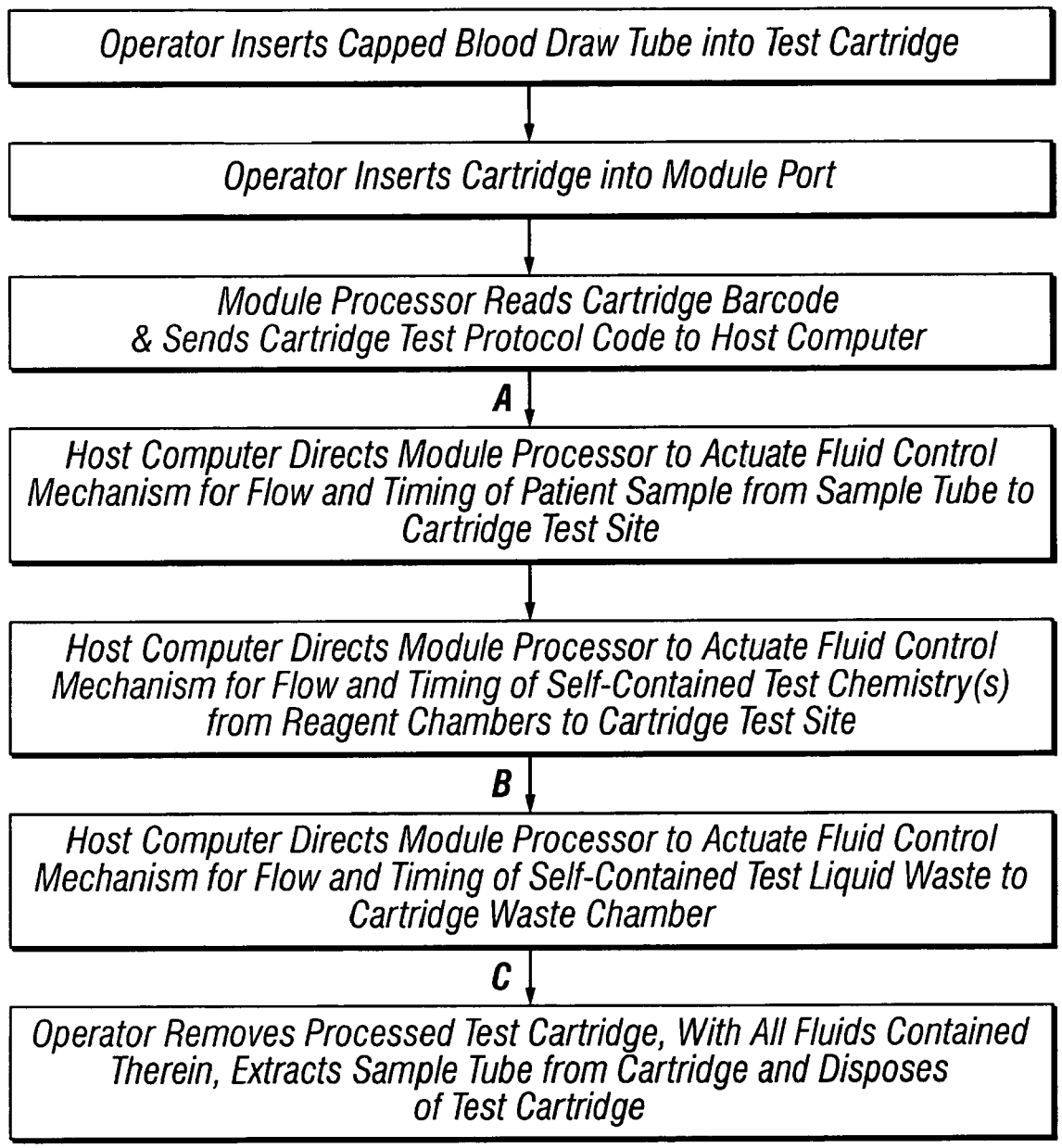
FIG. 3 is a flow chart illustrating one embodiment of a cartridge processing procedure implemented by logic resources of the present invention.
Figure 4:
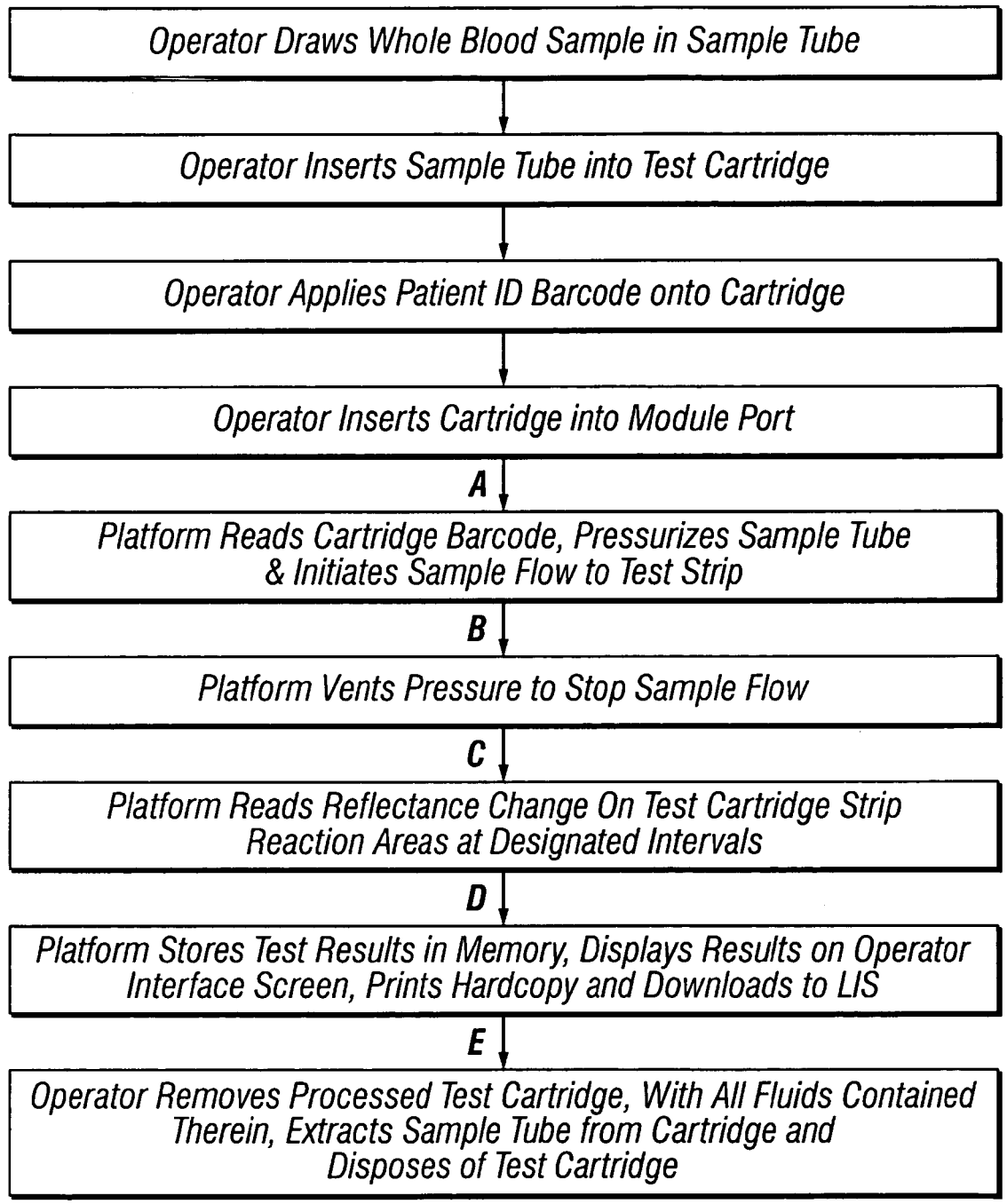
FIG. 4 is a flow chart illustrating one embodiment of an immunoassay operating procedure implemented by logic resources of the present invention.
Figure 5:
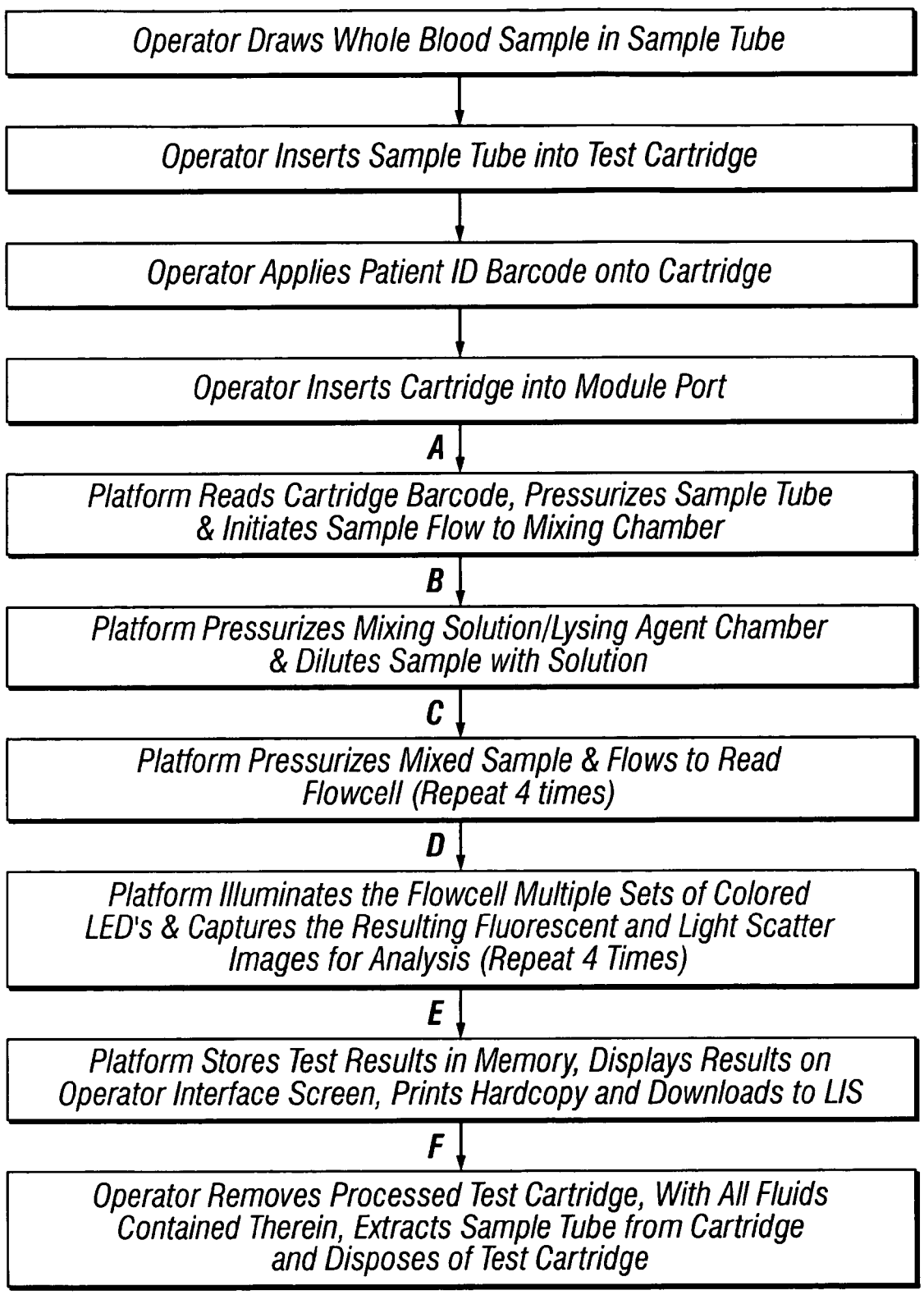
FIG. 5 is a flow chart illustrating one embodiment of a hematology operating procedure implemented by logic resources of the present invention.

FIG. 2 is a flow chart illustrating an overall methodology of implemented by logic resources 23. FIG. 3 is a flow chart illustrating one embodiment of a cartridge processing procedure implemented by logic resources 23. FIG. 4 is a flow chart illustrating one embodiment of an immunoassay operating procedure implemented by logic resources 23. FIG. 5 is a flow chart illustrating one embodiment of a hematology operating procedure implemented by logic resources 23.

As illustrated in FIG. 2, at block A, logic resources provides instructions that verify the barcode, the cartridge ID and the expiration date, block B. At each step, and at scheduled times, as shown at block C, sensor 18 with monitor device 21, monitors measurement chamber 19 to verify expected changes in electrical, optical properties, and the like. At block D, logic resources 23 provides instructions to compare sensor 18 response to a protocol and provide an indication if all are in an acceptable table range. In FIG. 3, logic resources 23 provides instructions to verifiy the bar-code at block A, monitor, along with monitor device 21, each step at block B, and confirm that a correct test protocol was followed at block C.

As illustrated in FIG. 4, logic resources 23 provide instructions to verify the patient barcode at block A, verify the cartridge, its expiration date, and that the sample is suitably positioned for sensor 18 at block B, verify sample present in a retention area at block C, verify sample and reagent washout at block D, and verify that a correct protocol sequence and its timing at block E. Referring to FIG. 5, logic resources 23 provides instructions to verifiy the patient ID at block A, verify the cartridge, its expiration date, detect the entrance of the sample into a mixing chamber on schedule at block B, detect the introduction of the sample into measurement chamber 19 at block C, verify successive movement of the sample through flow cell 12 at block D, verify adequate light and contrast for imaging quality at block E, and confirm that an overall protocol was followed at block F.

Figure 6A:
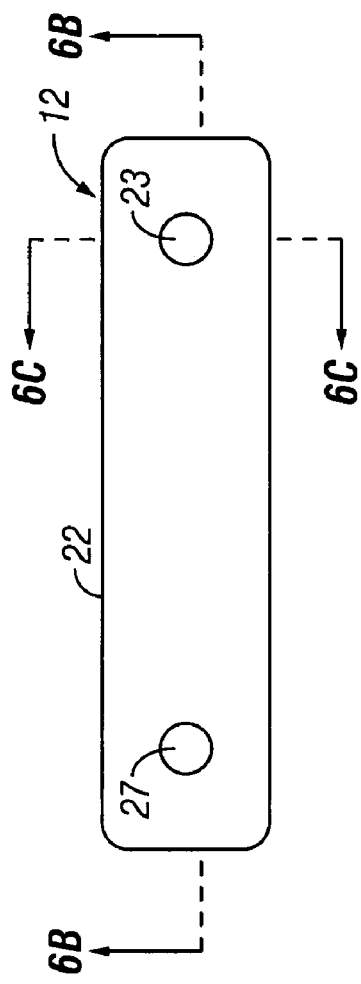
FIGS. 6(a)–6(c) illustrate one embodiment of a flow cell used in a fluid sample test in accordance with the present invention.
Figure 6C:
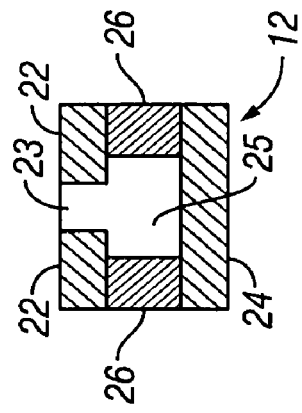
Figure 6B:
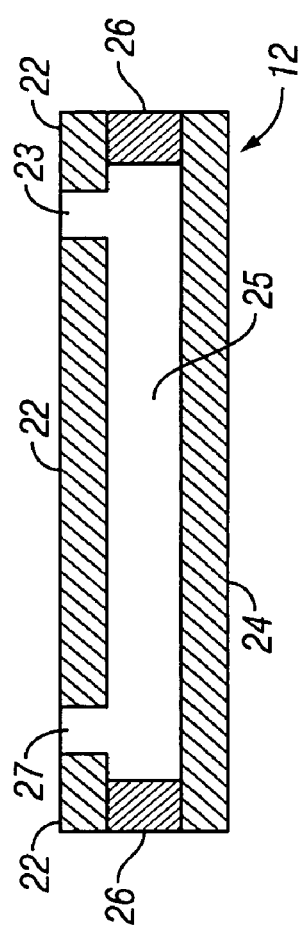

FIGS. 6(a)–6(c) schematically illustrate flow cell 12 for use in apparatus 10 in performing a test on a fluid sample in accordance with the present invention. Specifically, FIG. 6(a) is a top view of flow cell 12, FIG. 6(b) is a cross sectional view of flow cell 12 along cross sectional line B—B shown in FIG. 6(a), and FIG. 6(c) is a cross sectional view of flow cell 12 along cross sectional line C—C shown in FIG. 6(a). In one embodiment, flow cell 12 is made of transparent (to the sensor used) materials that are chemically inert to the test samples, reactive antibodies, reagents, and wash solution used in the test process.

Flow cell 12 includes a top plate 22, a bottom plate 24, and a gasket 26 sandwiched there between. By way of example, top plate 22 and bottom plate 26 are made of acrylic, and gasket 26 is made of a polyester film, e.g., the film commercially available under the trademark Mylar. An adhesive, e.g., ultraviolet curable acrylic is used to attach top plate 22, bottom plate 24, and gasket 26 together, thereby forming a channel 25. Openings or apertures are formed in top plate 22, communicating with channel 25 and serving as an inlet 23 and an outlet 27, respectively, of flow cell 12. Preferably, inlet 23 and outlet 27 are located adjacent to the two ends of channel 25. In accordance with a preferred embodiment of the present invention, a reactive antibody specific to an analyte to be tested using flow cell 12 is coated on the walls of channel 25.

Figure 7:
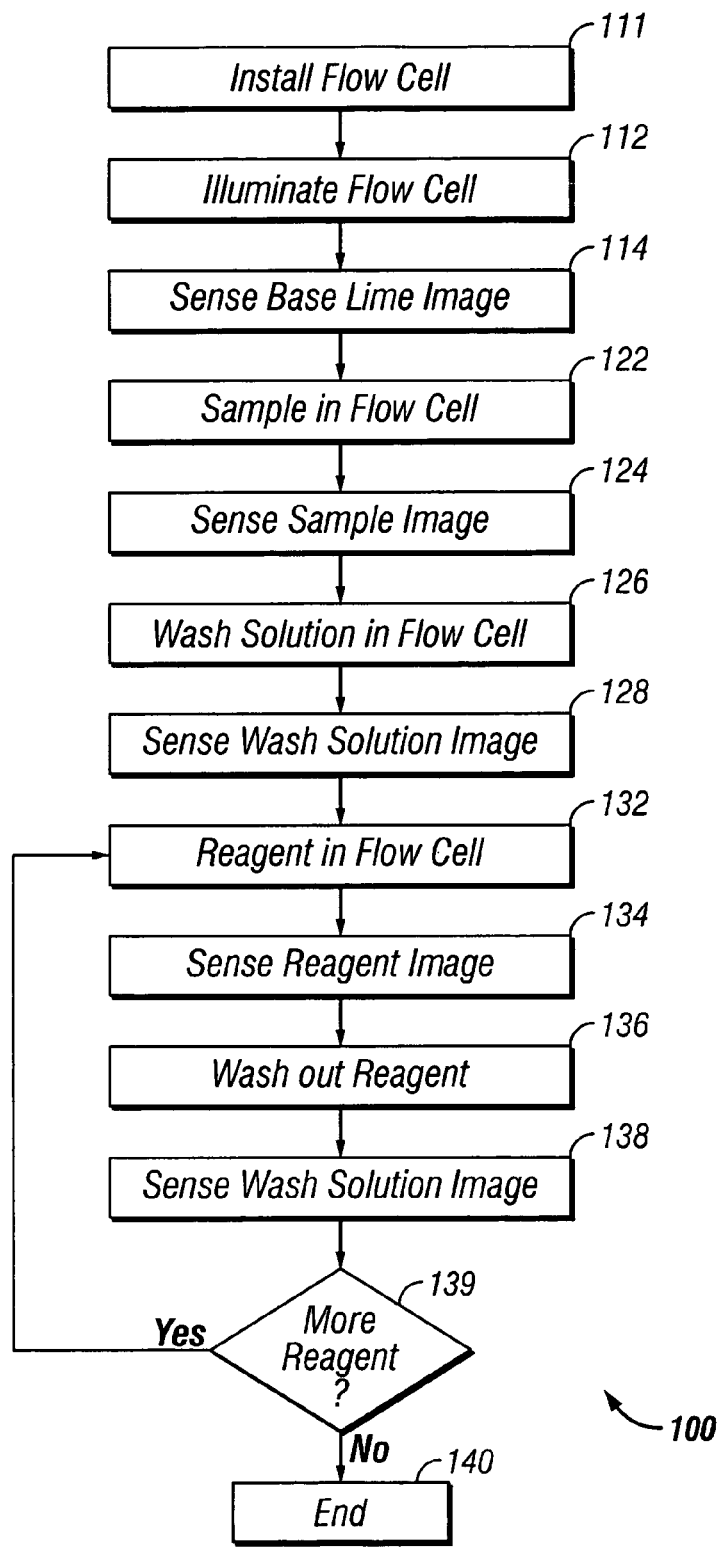
FIG. 7 illustrates a method for monitoring a test process in accordance with the present invention.

FIG. 7 is a flow chart illustrating a method 100 for monitoring a test process in accordance with the present invention. By way of example, the test process is performed on an apparatus functionally similar to apparatus 10 and flow cell 12 described herein above with reference to FIGS. #1 and 2, respectively.

Flow cell 12 has a reactive antibody coated thereon. The antibody is specific to the analyte to be tested. Preferably, the antibody is immobilized in specific regions on a surface of channel 25 in flow cell 12 during the production of flow cell 12. For example, in a pregnancy blood test, an antibody specific to human chorionic gonadotropin (hCG) is immobilized by hydrophobic adsorption in predetermined regions on the surface of channel 25 in flow cell 12. It should be understood that the antibody is not limited to being immobilized through hydrophobic absorption. Other means know in the art, either covalent or non-covalent means, can also be used for coating the antibody on flow cell 12.

In a step 111, flow cell 12 is installed on a test instrument, e.g., apparatus 10 shown in FIG. 1. In accordance with one embodiment, flow cell 12 is installed onto flow cell holder 11 of apparatus 10. In accordance with another embodiment, flow cell 12 is inserted into a test cartridge (not shown) and the test cartridge is installed on the test instrument.

In a step 112, light source 14 is turned on, illuminating flow cell 12 with incident light beam 15. The reactive antibody coated in flow cell 12 generates reflected light beam 17. In a step 114, photo sensor 18 detects reflected light beam 17. The digital image processor in photo sensor 18 processes the signal and generates a base line image data of light beam 17 reflected from the antibody coated in flow cell 12. Typically, the antibody coated in flow cell 12 will generate a uniform white image in photo sensor 18. However, dyes of various colors may be mixed with the antibody to generate base line image data of different characteristics, e.g., different intensities.

In a step 122, a predetermined amount of sample is introduced into flow cell 12. In a preferred embodiment, the sample flows into channel 25 of flow cell 12 through inlet 23 as a laminar flow. In one embodiment, a tube containing the sample is inserted into a sample dock of a test cartridge. The cartridge is installed on apparatus 10. A pump (not shown in FIG. 1) in apparatus 10 pumps the predetermined amount of the sample from the tube, through the cartridge and into inlet 23 of flow cell 12. A low-pressure pump is preferred in achieving the laminar flow of the sample into flow cell 12. However, this is not intended as a limitation on the scope of the present invention. Other mechanisms may be used to introduce the sample into flow cell 12. For example, the predetermined amount of the sample can be manually pumped into channel 25 of flow cell 12 through inlet 23 using a pipette. In flow cell 12, the sample is in contact and reacts with the reactive antibody coated of the surface of channel 25. The validity of the test result is sensitive to the exposure time of the analyte in the sample to the antibody. Therefore, it is important to closely monitor the time duration of the sample in flow cell 12 to ensure the quality of the test process.

In a step 124, photo sensor 18 detects and processes light beam 17 reflected from the sample in flow cell 12. Because of different light absorption and reflection characteristics, light beam 17 reflected from the sample in flow cell 12 and detected by photo sensor 18 has different color characteristics than that reflected from the reactive antibody and detected by photo sensor 18 in step 114. For example, in a blood test, the hemoglobin in blood significantly absorbs blue light. Therefore, the blood sample in flow cell 12 absorbs the light emitted from blue LED light source 14, thereby resulting a significant reduction in the intensity of reflected light beam 17. Photo sensor 18 detects a substantially dark image. This dark image indicates the presence of the blood sample in flow cell 12.

After a predetermined time exposure of the analyte in the sample to the antibody in flow cell 12, a wash fluid, which may be a liquid solution or a gas or airflow is introduced into channel 25 of flow cell 12 through inlet 23 in a step 126. Displaced by the incoming wash fluid, the sample flows out of channel 25 of flow cell 12 through outlet 27. The wash fluid preferably cleanses flow cell 12 of all of the sample except a portion of the analyte that has reacted with and is held by the antibody. In example of the blood pregnancy test, the fluid blood is cleansed out of flow cell 12. However, at least a portion of the hCG in the blood is held by the immobilized antibody coated on surface of channel 25 in flow cell 12.

In a step 128, photo sensor 18 detects and processes light beam 17 reflected from flow cell 12. As the sample is washed away from flow cell 12, the intensity of reflected light beam 17 gradually increases. The image data photo sensor 18 provides information regarding the efficiency and completeness of the sample wash out process in step 126. In accordance with one embodiment, the sample wash out process terminates after a predetermined time period. In accordance with another embodiment, the sample wash out process terminates in response to the intensity of light beam 17 increasing to a predetermined intensity, e.g., an intensity substantially equal to the intensity of light beam 17 in step 114 before the introduction of the sample into flow cell 12. This indicates that the wash out is substantially complete and flow cell 12 is substantially free of the sample.

In an embodiment with the wash fluid being a liquid solution, airflow is optionally introduced into channel 25 of flow cell 12 to disperse the remaining wash solution therein, i.e., to dry out flow cell 12. Preferably, a low-pressure air pump pumps the airflow into channel 25 of flow cell 12 through inlet 23. The airflow flows through channel 25 and out of flow cell 12 through outlet 27. In a preferred embodiment, a chemically inactive gas, e.g., an inert gas or nitrogen, is used to generate the airflow. Optionally, photo sensor 18 detects light beam 17 reflected from flow cell 12 to monitor the airflow. Furthermore, the airflow may have distinctive characteristics, including but not limited to pressure, flow rate, and the like.

After flow cell 12 is substantially cleansed of the sample, a solution having a reagent specific to the test is introduced into flow cell 12 to react with the analyte retained by the antibody coated on the surface of channel 25 in flow cell 12 in a step 132. In the blood pregnancy test example, a solution of colloidal gold labeled complimentary anti-hCG antibody is introduced into flow cell 12, where it binds proportionally to the retained analyte hCG. The red color of the colloidal gold serves as a marker or indicator of the reagent solution.

In a step 134, photo sensor 18 detects and processes light beam 17 reflected from flow cell 12. Light beam 17 reflected from the reagent solution in flow cell 12 generally has different color characteristics, e.g., intensity, than those reflected from the reactive antibody coated on the surface of channel 25 (step 114), from the sample in flow cell 12 (step 124), and from the wash fluid in flow cell 12 (step 128). The different color characteristics indicate different substances in flow cell 12.

After reacting with the retained analyte, the reagent solution is washed out in a step 136. Photo sensor monitors the effectiveness and completeness of the wash out process by detecting reflected light beam 17 in a step 138. In accordance with an embodiment of the present invention, the wash out of the reagent in step 136 and its monitoring in step 138 can be performed in substantially the same ways as steps 126 and 128, described herein above.

If the test process calls for another reagent to be introduced into flow cell 12 to react with the retained analyte (step 139), steps 132, 134, 136, and 138 are repeated. After all reagents are have been introduced into flow cell 12, reacted with the analyte therein, and washed therefrom, the test process terminates in a step 140.

It should be understood that, in accordance with the present invention, monitoring the test process is not limited to detecting and process light beams reflected from flow cell 12.

In accordance with an alternative embodiment, light source 14 is positioned on the opposite side of flow cell 12 from photo sensor 18. In this embodiment, photo sensor 18 detects and processes a light beam that propagates through flow cell 12. Accordingly, photo sensor 18 monitoring the test process by processing image data about the light absorption characteristics of the sample and reagents in flow cell 12.

In accordance with another alternative embodiment, light source 14 is so positioned with respective to flow cell 12 and photo sensor 18 that photo sensor 18 is not in that path of reflection light beam or absorption light beam. In this embodiment, photo sensor 18 detects and processes fluorescent light that is generated in flow cell 12. Accordingly, photo sensor 18 monitoring the test process by processing image data about the fluorescent light characteristics of the sample and reagents in flow cell 12.

In accordance with yet another alternative embodiment, apparatus 10 includes multiple light sources (not shown in FIG. 1). Such a multiple light source apparatus is capable of monitoring different test processes using image data formed from different light beams. Such versatility is advantageous for a point of care facility, e.g., a blood test instrument in a medical emergency room where a high level of test monitoring is demanede.

In accordance with the present invention, monitoring the test process is achieved by observing the intrinsic properties, e.g., light reflection characteristics, light absorption characteristics, or light fluorescence characteristics, of the test sample and reagents used in the test process. It does not require extrinsic data such as standard sample test results or secondary processing variables such as motor movement data. In addition, the process is monitored on a real time basis.

In various embodiments, the present invention provides a real time test process monitoring and quality control method and an apparatus for performing the test process. Compared with existing test monitoring processes, advantages of the monitoring method in accordance with the present invention include high reliability, cost efficiency, and time efficiency. The apparatus is simple, compact, and easily adaptable for different tests. The test methods and apparatus in accordance with the present invention are especially beneficial for the point of care test process, especially medical emergency room patient fluid sample test processes.

While the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention.

What is claimed is:

1. A method for determining the presence of at least one biological analyte that may be present in a liquid sample comprising:
   providing an apparatus for testing fluid samples that includes a flow cell with a measurement chamber, a monitor device that directly monitors flow of a sample and a reagent into measurement chamber, a light source that produces an incident beam directed to measurement chamber; and a sensor positioned to receive an output beam from the flow cell;
   introducing the liquid sample into the flow cell;
   using the monitor device to directly monitor flow of a sample and a reagent into the measurement chamber, the monitor device producing a signal indicative of an introduction and an exit of the sample and the reagent into the measurement chamber;
   in response to the monitoring determining if there is a sufficient amount of at least one of sample and reagent in the measurement chamber; and
   providing in a real time basis a sensing of a sample or a reagent without relying on information that originates outside the flow cell, wherein logic resources receive the signal from the monitor device and perform a comparison of a timing of the introduction and the exit of the sample to and from measurement chamber to produce a confirmation of a point in time of a valid reaction of the sample in measurement chamber.

2. The method of claim 1, wherein the information that originates outside of the flow cell includes a mechanical, electrical or photo within the apparatus outside of the flow cell.

3. The method of claim 2, wherein the mechanical information includes pump movement or valve rotation within the apparatus.

4. The method of claim 1, wherein real time is a frequency of measurement in a selected time period to insure that the reaction occurs in the selected time period.

5. The method of claim 4, wherein real time is in the range of 1 second to 1 minute.

6. A method for determining the presence of at least one biological analyte that may be present in a sample comprising:
   providing an apparatus for testing fluid samples that includes a flow cell with a measurement chamber;
   introducing the sample into the flow cell,
   using a monitoring device to directly monitor flow of at least one of a sample or a reagent into measurement chamber;
   in response to the monitoring determining if there is a sufficient amount of at least one of sample and reagent in the measurement chamber, the monitoring device producing a signal indicative of an introduction and an exit of the sample and the reagent into the measurement chamber;
   illuminating at least a portion of the measurement chamber and acquiring a digital image of an antibody; and
   producing an output signal indicative of the biological analyte in real time, wherein logic resources receive the output signal from the monitoring device and performs a comparison of a timing of the introduction and the exit of the sample to and from measurement chamber to produce a confirmation of a point in time of a valid reaction of the sample in measurement chamber.

7. The method of claim 6, wherein real time is a frequency of measurement in a time period to insure that the reaction in a selected time period.

8. The method of claim 6, wherein real time is in the range of 1 second to 1 minute.

9. The method of claim 1, wherein the sample is an analyte that contacts and reacts with an antibody in measurement chamber.

10. The method of claim 9, wherein an exposure time of the biological analyte in the sample to the antibody is a factor on whether or not a test result is a valid test result.

11. The method of claim 9, further comprising:
    monitoring a time duration of the sample in the flow cell.

12. The method of claim 11, wherein monitoring time duration of the sample in the flow cell is a factor used for the quality of a test process.

13. The method of claim 1, wherein the photo sensor detects and processes the output beam reflected from the sample in the sample chamber.

14. The method of claim 13, wherein the output beam is light intensity at specific wavelengths.

15. The method of claim 13, further comprising:
detecting different light absorption and reflection characteristics of the output beam.

16. The method of claim 15, wherein the different light absorption and reflection characteristics selected from at least one of, intensity, wavelength, polarity and scatter.

17. The method of claim 15, further comprising:
using the output beam to compare a timing and a sequence of changes during different times of biological analyte activity in the flow cell.

18. The method of claim 17, wherein a blood sample in the flow cell absorbs at least a portion of the incident beam and reduces an intensity of the output beam.

19. The method of claim 18, where the sensor detects a substantially dark image that is indicative of a presence of the blood sample in flow cell.

20. The method of claim 1, further comprising:
introducing a wash fluid to the reactive chamber after the biological analyte in the sample is exposed to the antibody.

21. The method of claim 20, wherein the wash fluid is selected from at least one of a liquid, gas or an airflow.

22. The method of claim 21, wherein the wash fluid displaces sample out of measurement chamber.

23. The method of claim 22, wherein the wash fluid removes the sample from measurement chamber except for a portion of biological analyte in the sample that has reacted with and held by the antibody.

24. The method of claim 23, wherein an intensity of the output beam increases as the sample is removed from measurement chamber.

25. The method of claim 23, wherein the sensor provides an indication of a completeness of sample removal from measurement chamber.

26. The method of claim 25, further comprising:
introducing an airflow into measurement chamber following introduction of the wash fluid into measurement chamber, wherein the wash fluid is a liquid.

27. The method of claim 26, further comprising:
utilizing the detector to monitor the airflow.

28. The method of claim 23, further comprising:
introducing a reagent to measurement chamber that reacts with biological analyte retained by the antibody in measurement chamber.

29. The method of claim 23, wherein light reflected from reagent solution in the flow cell has different characteristics than light reflected from reactive antibody in measurement chamber.

30. The method of claim 29, wherein light reflected from reagent solution in the flow cell has different characteristics than light reflected from wash fluid in the flow cell.

31. The method of claim 30, wherein the different characteristics are selected from, wavelength, intensity, capacitance, and conductivity.

32. The method of claim 31, wherein different wavelengths are an indicator of different substances in the flow cell.

33. The method of claim 1, wherein the sensor detects changes of the sample in measurement chamber selected from at least one of, light reflection characteristics, light absorption characteristics, light fluorescence characteristics, capacitance, and conductivity.

34. The method of claim 1, wherein the sensor monitors the test process by processing image data of light characteristics of the sample and reagents in the flow cell.

35. A method for determining the presence of at least one biological analyte that may be present in a liquid sample comprising:
providing an apparatus for testing fluid samples that includes a flow cell with a measurement chamber, a monitor device that directly monitors flow of a sample and a reagent into measurement chamber, a light source that produces an incident beam directed to measurement chamber and a sensor positioned to receive an output beam from the flow cell;
introducing the liquid sample into the flow cell that includes at least one bibulous material, at least a portion of flow in the flow cell being induced by the at least one bibulous material;
directly monitoring flow of a sample and a reagent into the measurement chamber, the monitor device producing a signal indicative of an introduction and an exit of the sample and the reagent into the measurement chamber;
providing in a real time basis a sensing of a sample or a reagent without relying on information that originates outside the flow cell, and
using logic resources to receive a signal from the monitor device and perform a comparison of a timing of the introduction and the exit of the sample to and from measurement chamber to produce a confirmation of a point in time of a valid reaction of the sample in measurement chamber.

36. A method for determining the presence of at least one biological analyte that may be present in a liquid sample comprising:
providing an apparatus for testing fluid samples that includes a flow cell with a measurement chamber;
introducing the sample into the flow cell that includes at least one bibulous material, at least a portion of flow in the flow cell being induced by the at least one bibulous material;
directly monitoring flow with a monitor device of at least one of a sample or a reagent into measurement chamber, the monitor device producing a signal indicative of an introduction and an exit of the sample and the reagent into the measurement chamber;
illuminating at least a portion of the measurement chamber and acquiring a digital image of an antibody; and
producing an output signal indicative of the biological analyte in real time, wherein logic resources receive the output signal from the monitor device and perform a comparison of a timing of the introduction and the exit of the sample to and from the measurement chamber to produce a confirmation of a point in time of a valid reaction of the sample in measurement chamber.

* * * * *